(12) United States Patent
Glaug et al.

(10) Patent No.: US 6,258,076 B1
(45) Date of Patent: Jul. 10, 2001

(54) DISPOSABLE ABSORBENT ARTICLE WITH WAIST BARRIER INCLUDING SKIN-FRIENDLY ADHESIVE

(75) Inventors: Frank S. Glaug, Chester Springs; Joan Rodgers, Brookhaven, both of PA (US)

(73) Assignee: Confab Services AG (CH)

( * ) Notice: Subject to any disclaimer, the term of this patent is extended or adjusted under 35 U.S.C. 154(b) by 0 days.

(21) Appl. No.: 09/318,972

(22) Filed: May 26, 1999

(51) Int. Cl.[7] ............................. A61F 13/15; A61F 13/20
(52) U.S. Cl. ..................... 604/387; 604/386; 604/385.01
(58) Field of Search ................. 604/358, 385.01, 604/385.03, 385.04, 385.05, 385.101, 385.11, 385.19, 385.201, 386, 389, 390, 401, 387

(56) References Cited

U.S. PATENT DOCUMENTS

| | | |
|---|---|---|
| D. 329,697 * | 9/1992 | Fahrenkrug et al. ............... D24/126 |
| 2,512,713 | 6/1950 | Cahill . |
| 2,742,903 | 11/1956 | Lightner . |
| 4,578,071 | 3/1986 | Buell . |
| 4,627,847 | 12/1986 | Puletti et al. . |
| 4,652,484 * | 3/1987 | Shiba et al. ......................... 428/286 |
| 4,738,677 | 4/1988 | Foreman . |
| 4,753,646 * | 6/1988 | Enloe .................................. 604/385 |
| 4,753,648 | 6/1988 | Jackson . |
| 5,026,364 | 6/1991 | Robertson . |
| 5,151,092 | 9/1992 | Buell et al. . |
| 5,304,160 | 4/1994 | Igaue et al. . |
| 5,445,627 | 8/1995 | Mizutani et al. . |
| 5,601,543 | 2/1997 | Dreier et al. . |
| 5,601,545 | 2/1997 | Glaug et al. . |
| 5,613,959 * | 3/1997 | Roessler et al. ...................... 604/364 |
| 5,662,633 * | 9/1997 | Doak et al. .......................... 604/378 |
| 5,700,255 | 12/1997 | Curro et al. . |

FOREIGN PATENT DOCUMENTS

| | | | |
|---|---|---|---|
| 850625 | 7/1998 | (EP) . | |
| 0 850 618 A1 | * 7/1998 | (EP) | ............................. A61F/13/15 |
| 0 850 626 A1 | * 7/1998 | (EP) | ............................. A61F/13/15 |
| 0 850 628 A1 | * 7/1998 | (EP) | ............................. A61F/13/15 |
| 873739 | 10/1998 | (EP) . | |
| 2 233 235 | * 1/1991 | (GB) | ............................. A61F/13/15 |
| WO 95/22306 | 8/1995 | (WO) . | |
| WO 97/17926 | * 5/1997 | (WO) | ............................. A61F/13/15 |
| WO 97/28773 | 8/1997 | (WO) . | |
| WO 00/37008 | 6/2000 | (WO) . | |

* cited by examiner

Primary Examiner—Aaron J. Lewis
Assistant Examiner—Michele Kidwell
(74) Attorney, Agent, or Firm—Caesar, Rivise, Bernstein, Cohen & Pokotilow, Ltd.

(57) ABSTRACT

A disposable absorbent article, e.g., a diaper, adult incontinent brief, shield, insert, pad, etc., with significantly improved leakage control, particularly for loose fecal matter. The article includes a barrier wall secured to at least the back waist portion of the article. The barrier wall includes a body-friendly pressure sensitive adhesive, which is arranged to be selectively exposed, if desired, to enable the adhesive to be releasably secured to the skin of the wearer. This securement forms a liquid resistant barrier to the egress of loose fecal material from the waist portion of the article. The adhesive is arranged to be covered when its use is not desired.

30 Claims, 5 Drawing Sheets

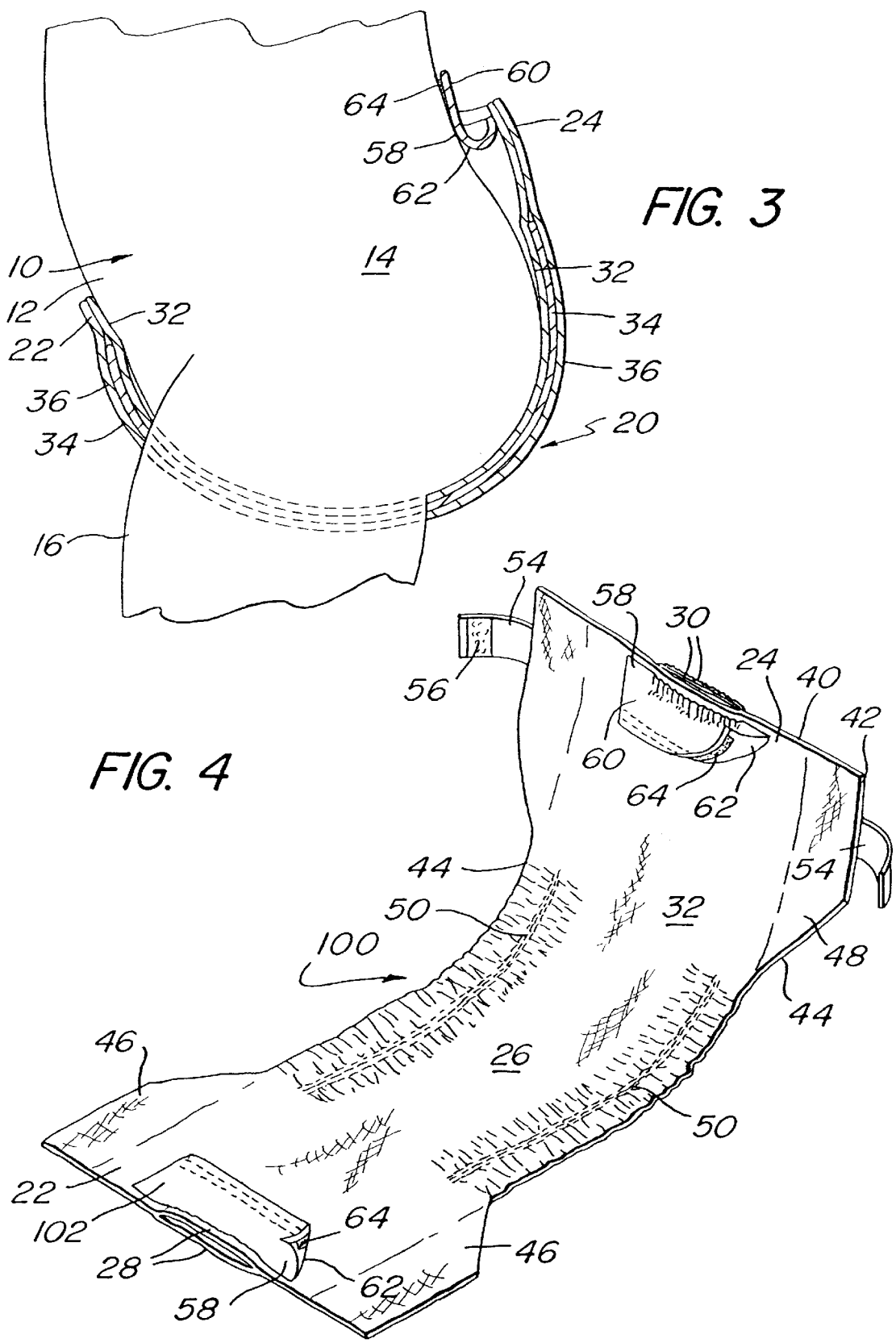

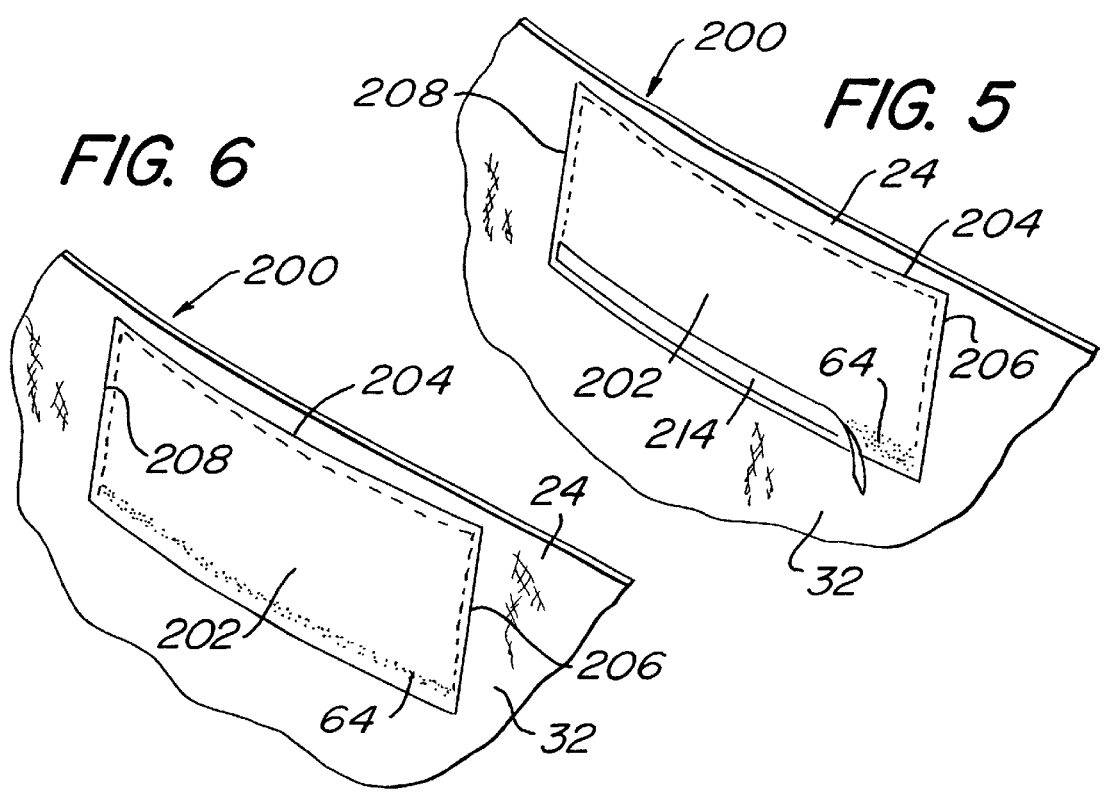
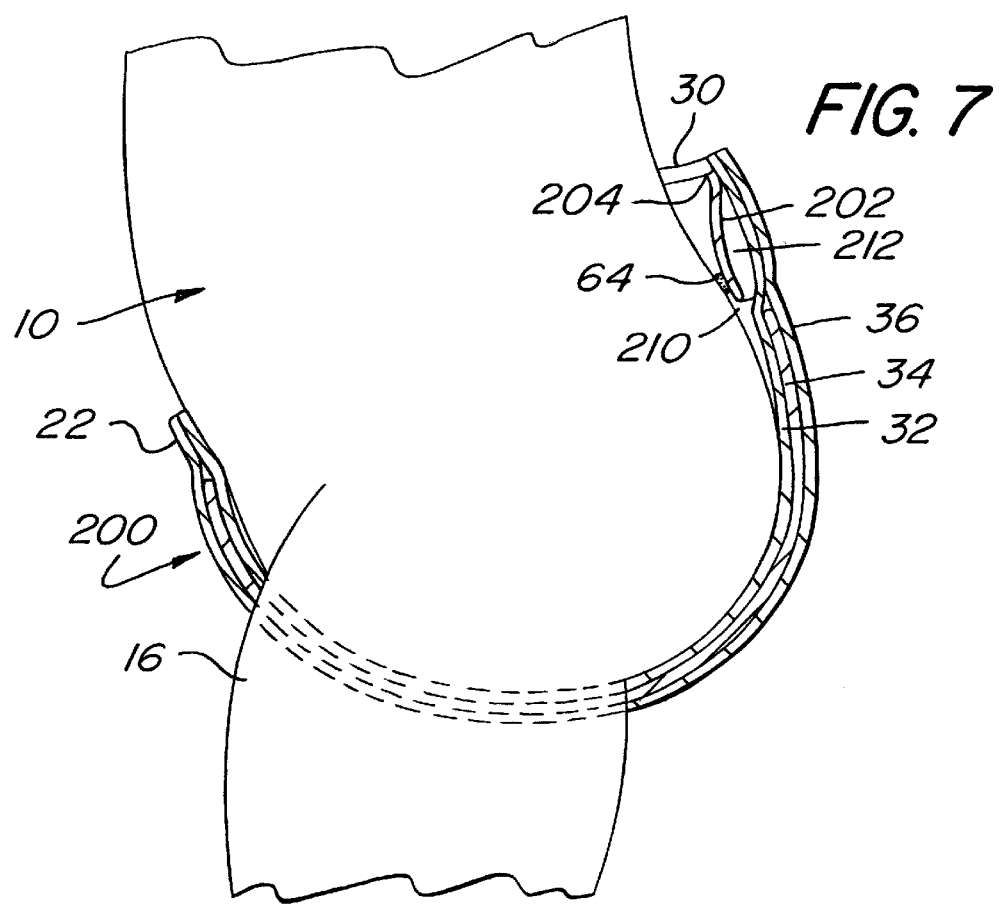

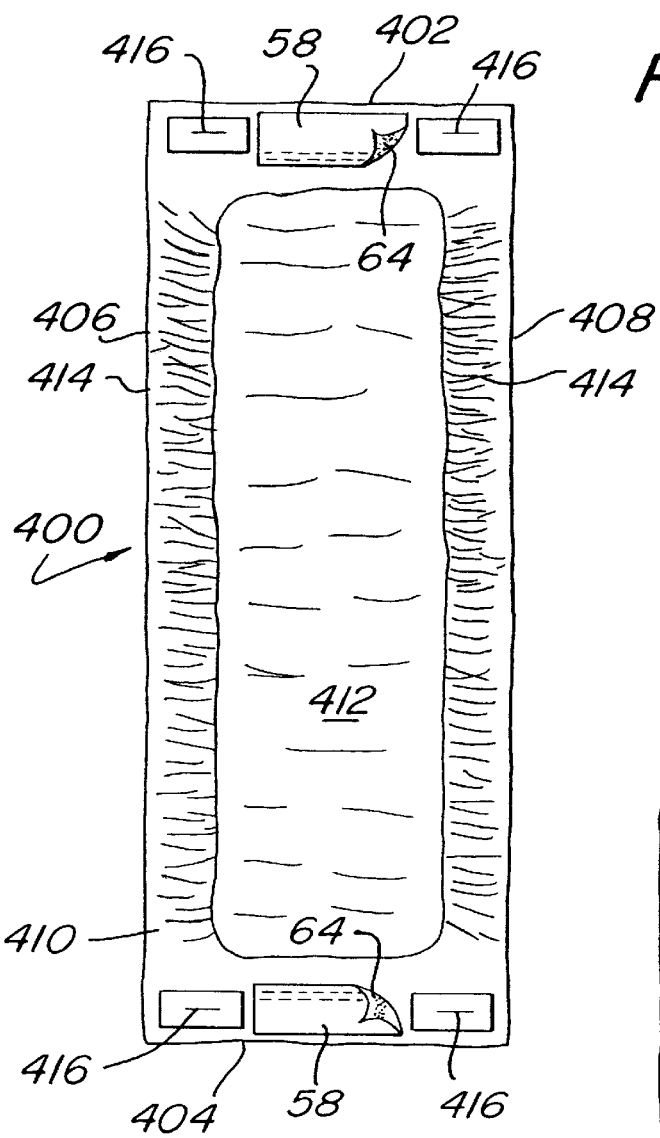
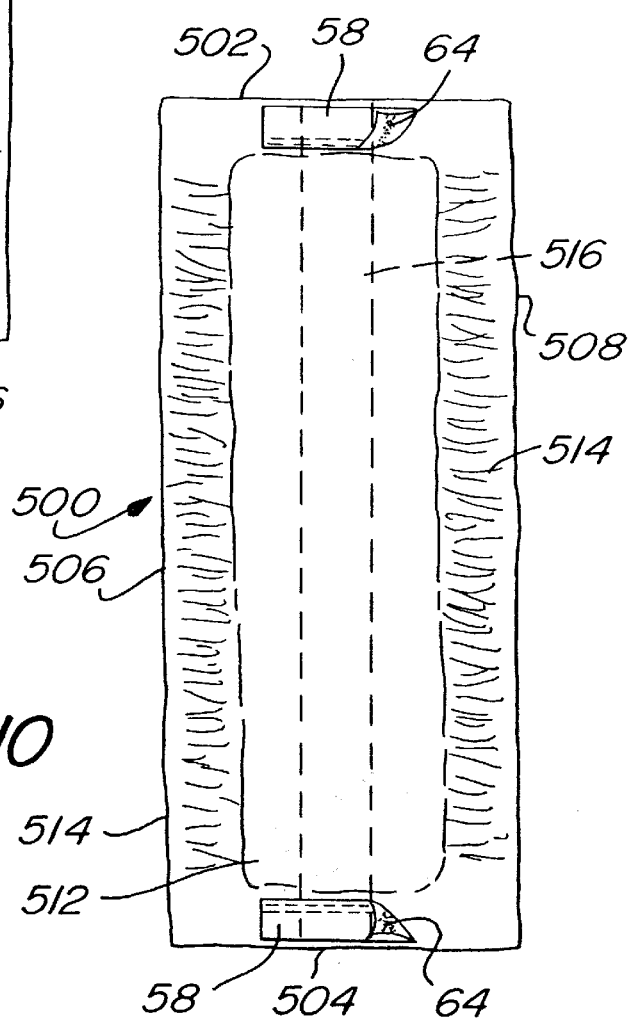

DISPOSABLE ABSORBENT ARTICLE WITH WAIST BARRIER INCLUDING SKIN-FRIENDLY ADHESIVE

FIELD OF THE INVENTION

This invention relates generally to disposable absorbent articles, e.g., diapers for infants and incontinent adults, and more specifically to disposable absorbent articles which include selectively operable means for providing a level of protection from waste matter leakage in the waist region of the garment heretofore not achieved.

BACKGROUND OF THE INVENTION

A principle function of absorbent articles, such as infant diapers and adult incontinent briefs, is to absorb and contain body waste. Such articles are designed to prevent body waste from soiling, wetting, or otherwise contaminating clothing or other articles, such as bedding, that come in contact with the wearer. A common mode of failure for such products occurs when body waste leaks out of the gaps between the article and wearer's waist to adjacent clothing due to the fact that it is not immediately absorbed within the article. This is most evident with loose fecal material that is not easily absorbed by the absorbent article.

Fecal waste, even in liquid form, usually has a higher viscosity versus urine and contains a certain degree of solids. The solids tend to block the small pores of the nonwoven coverstock and reduce penetration to the absorbent core underneath. In addition, the absorbent core is mainly designed to absorb urine and not solids. As a result, fecal material tends to "remain" on top of the coverstock. When the article is in a horizontal position, as in the case of the subject lying in a prone position, the combination of bodily pressure on the article and geometric position may force it out of the article, primarily out through the back waist region.

Infant diapers and adult incontinent briefs have significantly improved in the property of bodily waste containment; however, most developments have been in the area of urine containment. Liquid or solid fecal waste leakage is still a significant problem to the consumer. This type of messy leakage is more of a problem to the consumer than urine leakage. In most cases, more work and time is needed to soak, wash and clean soiled clothing as a result of fecal waste leakage. A significant improvement in this area would be greatly valued by the consumer.

Various disposable absorbent articles exist today for absorbing waste material of infants and adults. One of these is a disposable diaper that is fitted on the baby by the mother or caretaker. How tightly the diaper is wrapped around the baby's waist depends on the mother or caretaker. However, no matter how tight the mother or caretaker may attach the diaper on the infant, a perfect seal is not formed at the back waist area of the diaper to prevent fecal waste from leaking out. This is especially so if the infant is laying on his/her backside and the fecal waste that is emitted is fluid in nature and significant in volume.

Other waist barrier features have been identified for disposable diapers, such as elastic waistcaps for reducing the leakage of body exudates from the diaper waist region. Examples of such diapers are disclosed in U.S. Pat. No. 4,738,677 (Foreman) and U.S. Pat. No. 5,026,364 (Robertson).

Disposable diapers containing pockets or waist flaps are disclosed in U.S. Pat. No. 4,753,646 (Enloe), U.S. Pat. No. 5,304,160 (Igaue et al.), and U.S. Pat. No. 5,601,543 (Drier et al.).

The concept of utilizing waist elastic to contain bowel movement is disclosed in U.S. Pat. No. 5,151,092 (Buell et al.), and U.S. Pat. No. 5,700,255 (Curro et al.).

The use of additional absorbent material at the waist area of disposable absorbent articles is disclosed in U.S. Pat. No. 5,601,545 (Glaug et al.).

The use of adhesives that attached to the body in sanitary napkin designs are disclosed in U.S. Pat. No. 5,445,627 (Mizutani et al.), U.S. Pat. No. 4,753,648 (Jackson), U.S. Pat. No. 2,742,903 (Lightner), and International Publication No. WO 97/28773, issued Aug. 14, 1997.

U.S. Pat. No. 4,627,847 (Puletti et al.) discloses a hot melt adhesive waste barrier, and U.S. Pat. No. 2,512,713 (Cahill) discloses a rectal bandage.

While the prior art disposable absorbent articles may be generally suitable for their various intended purposes, there still exists a need for a disposable absorbent article, e.g., an infant diaper, adult incontinent brief or shield, etc., that is both effective and efficient in containing fecal waste (primarily in liquid form) from leaking out the waist opening of the article. In this regard, prior art disposable articles focus on either improving the elastic gathering at the waist area (waistband) or adding a pocket (waist flap) with elastic means to contain fecal waste, neither of which has solved the problem of liquid fecal leakage sufficiently well. In this regard, the prior art elastic waistbands have not eliminated or significantly reduced liquid fecal waste leakage for several reasons. In particular, elastic tension at the waist cannot be tightened high enough to eliminate leakage (too high elastic tension will cause significant discomfort to the user and red marking/irritation to the body). Also, elastic memory will reduce over time, especially under high stress conditions (loss in elastic memory will allow gaps to form in which fluid or liquid mass can leak out). Further still, elastic gathering of materials creates corrugations within the material that could allow fluid or liquid mass to pass through the small openings and cracks.

The addition of pockets or waist flaps have not eliminated or significantly reduced liquid fecal waste leakage for disposable absorbent articles either. In particular, these pockets may catch a portion of the fecal waste that is expelled, however the majority of it bypasses this type of barrier system. This is especially true if the fecal waste is in liquid form, is under high pressure or stress (e.g., the absorbent article is squeezed against the body), is significant in volume and is rapidly expelled or ejected from the body.

Accordingly, a need still exists for a disposable absorbent article which is resistant to leakage of liquid or loose fecal matter at the waist area.

OBJECTS OF THE INVENTION

It is a general object of this invention to provide a disposable absorbent article which addresses the needs of the prior art.

It is an another object of this invention to provide a disposable absorbent article that is secured to the body in the waist region to form a containment barrier to loose fecal matter.

It is an another object of this invention to provide a disposable absorbent article that is adhesively secured to the body in the waist region without sacrificing wearing comfort.

It is another object of this invention to provide a disposable absorbent article with preselected segments of the inner waist region having portions which may be selectively used, if desired, to adhesively attach the article to the wearer's body and thereby form a waste barrier thereat.

It is still another object of this invention to provide a disposable garment with a pocket in the waist region wherein the pocket is formed by a flap section attached to the inner surface of the diaper and wherein preselected segments of the flap are adhesively attached to the wearers body, thereby forming a dual functioning containment barrier.

It is yet another object of the present invention to provide a disposable garment with a preselected area comprising a layer of pressure sensitive adhesive covered with a soft, absorbent pliable release liner.

Another object of the present invention is to provide a means for attachment of disposable garments to the body of the wearer, wherein the means is in the form of a layer of pressure sensitive adhesive to establish an adhesive bond with the skin and which is maintained under hot, moist conditions, yet is readily and easily peeled away upon removal of the garment for disposal.

SUMMARY OF THE INVENTION

A disposable absorbent article, e.g., a diaper, an absorbent shield, an absorbent insert, etc., arranged to be worn by a living being to trap and collect loose or liquid waste products of the being. The disposable absorbent article basically comprises a flexible chassis or body member, a first barrier panel, and a first exposable skin-friendly adhesive.

The chassis is absorbent and has an inner surface, an outer surface, a pair of side portions, a front waist portion, a rear waist portion, and a crotch portion. The chassis is configured to be worn so that the crotch portion is between the legs of the being, and with the inner surface of the chassis directed toward the being's skin, e.g., the front waist portion being disposed adjacent the being's lower abdominal region and it's rear waist portion being disposed adjacent being's lower back region.

The first barrier panel is mounted on the inner surface of the chassis at the rear waist portion. The first selectively exposable, skin-friendly adhesive is located on the first barrier panel and is arranged to be selectively exposed, if desired, to enable it to engage the adjacent skin of the being. When this has occurred, the first barrier panel and the first selectively exposable, skin-friendly adhesive form a liquid-resistant seal with the being's skin to thereby impede the egress of the loose or liquid waste from the rear waist portion of the disposable absorbent article.

In one preferred embodiment the first barrier panel is in the form of a flap having an inner surface and an outer surface. The flap is secured to the inner surface of the body member so that the inner surface of the flap confronts the inner surface of the body member. The first selectively exposable, skin-friendly adhesive is located on the inner surface of the flap. The flap is movable to an operative position, wherein the inner surface of the flap is exposed to enable the first selectively exposable, skin-friendly adhesive to be brought into engagement with the skin of the being for releasable attachment thereto.

In another preferred embodiment the first barrier panel is secured to the inner surface of the body member at the back waist portion to form a pocket. The pocket has an outer surface on which the first selectively exposable, skin-friendly is located. A removable cover strip, e.g., a multi-layer member having a skin-friendly outer surface and a peelable inner surface, is releasably mounted on the first selectively exposable, skin friendly adhesive.

The disposable absorbent article may include a moisture pervious inner or top sheet, a liquid absorbent core, and a liquid impervious outer cover. In addition, it may include a second barrier panel located at the front waist portion and on which a second selectively exposable skin-friendly adhesive is located. The second selectively exposable, skin-friendly adhesive is also arranged to be selectively exposed, if desired, to enable it to engage the adjacent skin of the being, whereby the second barrier panel and the second selectively exposable, skin-friendly adhesive form a liquid-resistant seal with the being's skin to thereby impede the egress of the loose or liquid waste from the front waist portion of the disposable absorbent article.

DESCRIPTION OF THE DRAWING

FIG. 3 is a partial sectional illustration of the embodiment of the invention of FIG. 1 shown in place on the body of an infant;

FIG. 4 is an isometric view of a preferred embodiment of a second type of disposable absorbent article, e.g., a diaper without any standing leg cuffs, constructed in accordance with this invention to provide a liquid fecal material barrier at the waist;

FIG. 5 is an isometric view of the waist portion of another alternative preferred embodiment of this invention, e.g., a disposable absorbent article utilizing a variant of the fecal material barrier for the waist from that shown in FIGS. 1 and 4, and with the means forming that barrier being shown in a state before it is ready for usage;

FIG. 6 is a view similar to FIG. 5 but showing the means for forming the fecal material barrier in its operative state ready for use;

FIG. 7 is an illustration like that of FIG. 3 but showing the use of the embodiment of the invention of FIG. 5;

FIG. 9 is a reduced plan view of still another preferred embodiment of one type of disposable absorbent article, e.g., a belt-supported garment or shield, constructed in accordance with this invention to provide a fecal material barrier at the waist;

FIG. 10 is a reduced plan view of yet another preferred embodiment of one type of disposable absorbent article, e.g., an "extra" absorbent beltless pad, constructed in accordance with this invention to provide a fecal material barrier at the waist.

DETAILED DESCRIPTION OF THE PREFERRED EMBODIMENT

Figure 1:
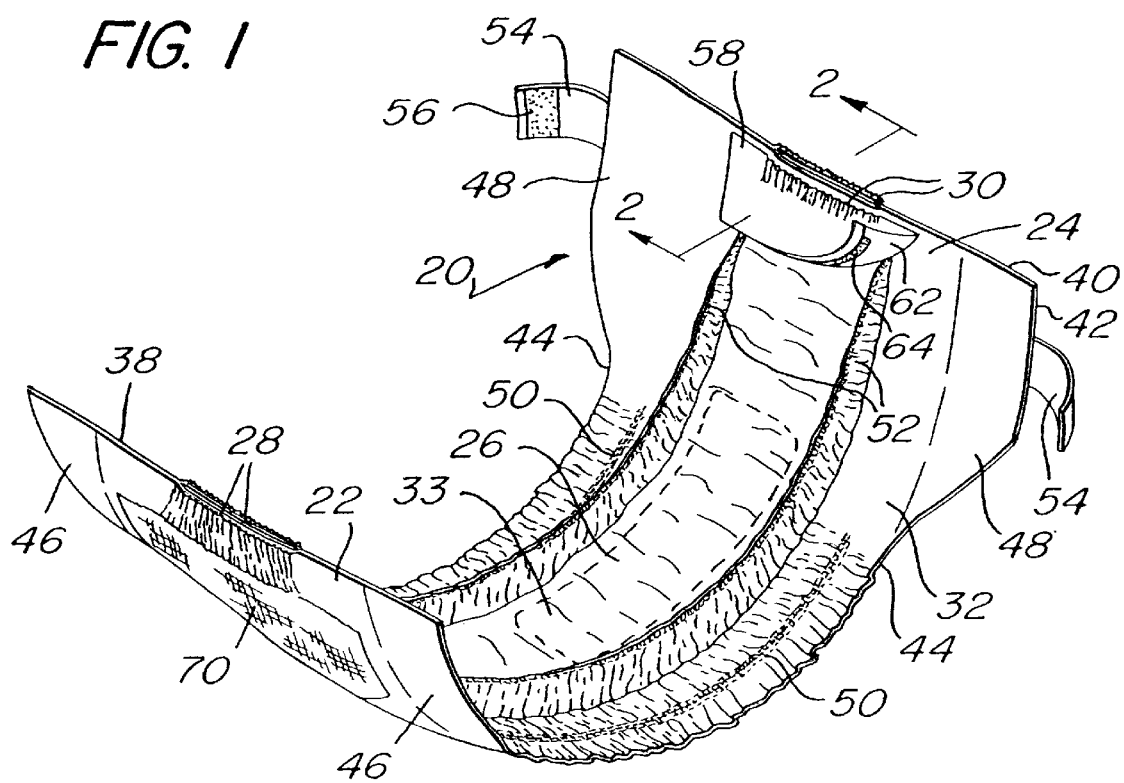
FIG. 1 is an isometric view of a preferred embodiment of one type of disposable absorbent article, e.g., a diaper having standing leg cuffs, constructed in accordance with this invention to provide a fecal material barrier at the waist.

Referring now to the various figures of the drawing wherein like reference characters refer to like parts, there is shown in FIG. 1 a disposable absorbent article 20 constructed in accordance with one embodiment of this invention. The article 20 of FIG. 1 is in the form of a child's diaper comprising a front waist portion 22, a back waist portion 24, and a crotch portion 26. The front waist portion includes an elastic section 28 formed by an elastic member. The rear waist portion also includes an elastic section 30 formed by an elastic member. The elastic member is secured in place by a suitable elastic adhesive, e.g., a pressure sensitive hot melt with a viscosity of 2,400 centipoise at 325 degrees F. The elastic member can be attained from General Foam, of Paramus, N.J., and the elastic adhesive from National Starch and Chemical Company, Bridgewater, N.J.

Although the article 20 is illustrated and described as a diaper, the present invention can be utilized in other types of absorbent disposable articles, e.g., adult incontinence products, or the like, some of which will be illustrated and described in other embodiments to follow. It should be pointed out that as used herein the term "disposable" means that article is designed to be used until soiled, either by urination or otherwise, and then discarded, rather than being washed and used again.

Figure 2:
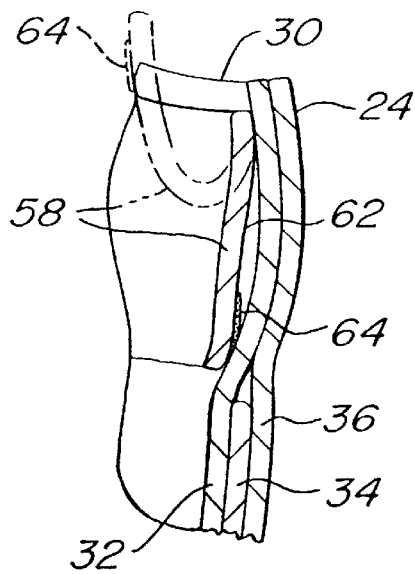
FIG. 2 is an enlarged sectional view taken along line 2—2 of FIG. 1.

The diaper 20 is of generally conventional construction, except for the inclusion of the means for preventing the egress of liquid fecal materials from the waist portion of the article. That means will be described in detail later. Prior to describing that means a brief description of the other portions of the diaper will now be discussed. To that end and as best seen in FIG. 2, the diaper 20 basically comprises a body-side liner or topsheet 32, fluid acquisition layer 33 (sometimes called an "acquisition or surge layer"), a liquid absorbent structure or core 34, and an outer cover or backsheet 36. The topsheet 32 is arranged to face toward the body of the user, when the diaper is in place, with the backsheet facing away from the wearer. The topsheet is superimposed over the backsheet, with the absorbent core interposed therebetween. A fluid-acquisition layer 33 is preferably located on top of the core and under the topsheet to facilitate the passage of liquid waste into the core for absorption thereby. The topsheet 32 and/or backsheet 36 can be any suitable shape and dimensions for other designs or constructions, as will be clear from the other embodiments disclosed herein.

The backsheet 36 comprises front edge 38, a back edge 40, and a pair of side edges 42. Each side edge includes a central, cut-out portion 44 to define a respective leg cut out. A pair of front ear portions 46 are located on opposite sides of the backsheet at the interface of the front edge of the backsheet and the two side edges 42. A similar pair of rear ear portions 48 are located on opposite sides of the backsheet at the interface of the rear edge of the backsheet and the two side edges 42. The crotch portion 26 of the diaper is located between the leg cut-outs.

The topsheet 32 may be of the same shape as the backsheet 36 or of a different shape. In the embodiment of the diaper 20 shown herein the topsheet 32 is of a generally rectangular shape and is bonded to the backsheet 36 around its entire periphery, with the absorbent material core 34 interposed therebetween. The backsheet and topsheet can be joined together in any suitable manner, e.g, by adhesive bonding. The adhesives can be applied in any manner such as by spraying, slot-coat extrusion, printing, or the like. The applied adhesive can be in any desired configuration or design, such as continuous or discontinuous beads, continuous or discontinuous swirls, meltblown patterns, spray patterns, or the like. Alternatively, the joining of layers and structures can be accomplished by heat sealing, ultrasonic bonding, or the like.

A fluid-acquisition layer 33 serves to manage, transport, accommodate and/or direct high volumes and high flow rates of urine into the absorbent core 34. The fluid-acquisition layer 33 can be a through-air bonded/carded web, a spun-bond bi-component non-woven web, a web of cross-linked cellulosic fibers, apertured 3D film or the like. One particular suitable material is available from PGI Nonwovens, Landisville, N.J., and has a total basis weight of 40 gsm, with high denier (10 denier) bi-component fibers situated on the top (facing the topsheet) and low denier (6 denier) bi-component fibers situated on the bottom (facing the core). The bi-component fibers are made of a polypropylene inner core and polyethylene outer sheath. The fluid-acquisition layer 33 is adhesively secured in place to the cover sheet by any suitable construction adhesive or hydrophillic adhesive, e.g,. Cycloflex adhesive available from National Starch and Chemical, Bridgewater, N.J.

Each lateral side edge 42 of the diaper 20 is elasticized by means of plural, e.g., three, longitudinally extending elastic, e.g., LYCRA 940 decitex, threads or strands 50 disposed along the length of the cut away portion 44 of that side edge. The strands may be attained from E.I. DuPont de Nemours and Company, Wilmington, Del., and are held in place by a suitable elastic adhesive, such as that used to hold the elastic member of the waist portion in place. The elastic adhesive is intermittently applied along the top sheet to allow the diaper to be actively stretchable along the leg cut outs and not all the way to the edges of the respective waist portions, thereby enable the diaper to closely conform about the legs of the wearer for impeding the egress of waste material from the crotch region, as in conventional executions. Other arrangements can be used to elasticize the sides of the crotch portion of the diaper. For example, in lieu of plural longitudinally extending elastic strands 50, multiple strands of elastic material can be arranged in other orientations, intersecting, diagonal, or any combination thereof, or can be a film or laminate of various types of elastomeric material.

The backsheet 36 or outer cover is preferably formed of a laminated sheet of a non-woven material and film (with the non-woven side positioned as the outermost layer). Such material should be hydrophobic, soft in texture, and strong in tensile strength. One particularly suitable material is a spunbond-meltblown-spunbond (SMS) web having a basis weight of about 15 gms per square meter (gsm), available from AVGOL Nonwoven Industries LTD., Holon, Israel. The spunbond layer is made of polypropylene fibers. Such composites provide the dual advantages of liquid barrier properties of film along with a soft, flexible outer fabric texture. The non-woven outer cover can also be made of other suitable cloth-like materials, e.g., spunbond or thermalbond non-woven web made of either polypropylene, polyethylene, polyester, bi-component fibers (polyethylene/polypropylene or polyethylene/polyester), or any combinations of these fibers. Various multiple layer configurations or fiber denier variations may be used. Another example includes hydro-entangled non-woven webs, which may contain some cotton and/or rayon fibers blended in with thermal-plastic fibers. Cellulose fibers can also be blended in at small percentages to reduce cost. Still another example is a non-woven outercover made of stretchable or elastic materials, such as elastomeric composites of non-woven(s) and elastic membranes or a single layer of elastic material. The elastomeric composite can comprise of an inner layer of pre-stretched extruded elastic film sandwiched between and attached to a pair of non-woven webs. The non-woven webs may consist of spunbond web, thermalbond web, or a combination of the two. Preferably, the elastic film is made of synthetic rubber and the non-woven made of spunbond polyethylene.

Other materials for forming the backsheet 36 may include polyethylene films, polypropylene films, co-extruded films (polyethylene and ethylene vinyl acetate), co-polymer films (polyethylene/polypropylene), and polylaminates (polypropylene nonwoven and polyethylene film). Still another example is a film made of a "breathable' microporous polyethylene. Suitable breathable films are available from Exxon Chemical Company, Buffalo Grove, Ill. This material allows water vapor to pass through it over time, while being impervious to liquid water. The water vapor transmission rate may range from 200–2000 grams per square meter per 24-hour period.

In order to enable urine to quickly and efficiently pass through the topsheet and into the underlying absorbent core 34 for trapping therein, the topsheet 32 is preferably liquid permeable. In particular, the top sheet may be selected from a variety of textile-like films and fabrics. Suitable fabrics include non-woven materials that are pervious to liquid, soft and pliable. Preferred non-woven materials include spun-bond polypropylene; spunbond polyethylene; bi-component spunbond fibers (polypropylene and polyethylene) thermally bonded webs of staple fibers preferably polypropylene or sheath/core bi-component fibers having a core of polyester or polypropylene and a sheath of polyethylene. To enhance the fluid control properties of the aforementioned liners, surfactants or wetting agents typified by Triton X-100 (Rohm & Haas, Philadelphia, Pa.) may be applied to the fluid receiving zones of the liner selectively having the outer zones untreated to reduce migration excreted fluid such as urine into the outer diaper regions leading to diaper leakage.

If desired, the top sheet 32 may be formed of a liquid impermeable material having plural apertures or pores extending therethrough so as to make the material liquid permeable.

The absorbent core 34 is a rectangular member which is centered in the diaper and extends close to the front waist edge and close to the back waist edge. The core can be made up of any suitable absorbent material, as well as combinations of different types of absorbent material(s). For example, the absorbent core may be formed of a mixture of pulp fluff and superabsorbent particulate (SAP) wrapped in a liquid permeable tissue wrap. Examples of SAP include polyacrylamides, polyvinyl alcohol, polyacrylates, various grafted starches, and the like. A desired superabsorbent material is a cross-linked polysodium acrylate, which can be purchased from Chemdal Corporation, Palatine, Ill., under the trade name ASAP 2102. The superabsorbent materials can be in various geometric forms, such as various shaped particles, fibers, foams, and layers. The fluff and SAP are present in a ratio of about 10 gms. SAP and 19 gms. fluff, for a size 4 diaper, and have a core density range of about 0.14 to 0.20 grams per cubic centimeter.

Moreover, the core 34 can be a single, integral absorbent structure, or can comprise a plurality of individual separate absorbent structures and/or absorbent materials that are operably assembled together. It can also consist of airlaid non-woven web that contains superabsorbent particles and/orsuperabsorbentfibers, polymeric binderand cellulose pulp fibers. In one exemplary embodiment the absorbent core is sandwiched between two plies of tissue, is aligned on top of the backsheet and adhered down with construction adhesive. The tissue has a basis weight of 17.1 gsm. Suitable tissues are available from Cellu Tissue Corporation, East Hartford, Conn. The absorbent core is centered along the transverse direction and registered in the machine (longitudinal) direction within the diaper's chassis.

The diaper 20 also includes a pair of conventional "standing leg gathers" or cuffs 52 or liquid-impervious gaskets to provide leakage control in the crotch region. The standing leg gathers are located so that they extend along the leg opening region of the diaper as disclosed in U.S. Pat. No. 4,695,278 (Lawson) and U.S. Pat. No. 4,795,454 (Dragoo), both of which are incorporated by reference herein. Each standing leg gather is elasticized and extends from the edge of the front waist portion to the edge of the rear waist portion and along a respective side marginal edges of the core 34 and upstanding from the topsheet 32.

The diaper 20 is arranged to be held in place on the body of the wearer 10 as shown in FIG. 3 in a conventional manner, e.g., by means of a pair of fastening tabs or tapes 54 projecting outward from the back ear portions 48 adjacent the back waist portion of the diaper. In particular, each tab 54 includes a patch 56 of a myriad of small hooks on its underside surface. Each patch is arranged to be releasably secured to a "landing zone" portion 70 on the outer cover in the front waist region of the diaper. The landing zone is located at a position so that when the diaper is folded in half with the front waist portion disposed opposite the back waist portion, the landing zone 70 will be aligned with the tabs 54. The landing zone 70 basically comprises a rectangular panel of whose outer surface comprises a myriad of small loops arranged to be engaged by the small hooks of the patch 56 of each fastening tab. When the diaper is in place on the person with the front waist portion and front ear portions 46 disposed over the lower abdomen 12, the back waist portion disposed over the lower back and buttocks region 14, and the crotch portion between the legs 16, each tab 54 may be brought into engagement with the a portion of the landing zone closest to that tab on the front portion of the diaper so that the myriad of hooks on the patch 56 engage the myriad of loops of the landing zone 70 to releasably secure the tape thereto. Any suitable multihook and multiloop materials may be used. Particularly suitable microreplicated hook patches 56 containing 900 pin density mushroom-shaped hooks are available from 3M Corporation, St. Paul, Minn., under the model designation CS-200, while particularly a suitable Knitted Loop Tape, designated as KLT, is made up of a warp knitted polyester fabric bonded to a polyolefin film backing coated with pressure sensitive adhesive is available from 3M Corporation, St. Paul, Minn.

Alternatively the tabs 54 may be in the form of adhesive tapes, such as those available from 3M Corporation, St. Paul, Minn., and the landing zone may be formed of a polyester film with a pre-applied adhesive in a selected print pattern, such as also available from 3M Corporation, St. Paul, Minn.

In accordance with this invention, the diaper 20 also includes a panel-like flap (to be described later), which is arranged to be adhesively secured to the skin of the wearer, if desired, to to form a barrier wall 58 in rear waist section of the diaper. The use of the flap to form the barrier wall is optional, albeit desirable. When used, the barrier wall's adhesive engagement with the skin of the wearer at the back waist region forms an intimate and fluid-proof interface with the skin of the wearer at the waist area to preclude the egress of liquid fecal waste material from that portion of the diaper under various levels of activity and positions, yet which is non-irritating and can be readily broken when desired to remove the diaper from the wearer.

As best seen in FIGS. 1 and 2 the barrier wall 58 comprises an elongated, e.g., rectangular, panel of a body-friendly, liquid impervious material, such as a piece of fabric, film, or foam. The panel does not have to be totally liquid impervious, e.g., it may be hydrophobic and breathable in nature. The material strip may also have elastic properties to act as a functional waistband for the diaper. One particularly suitable material for the barrier wall 58 is a poly laminate material under the model designation XLAM 9B-396, which is presently available from Huntsman Packaging, Newport News, Va. The panel 58 has an outer surface 60 and an inner surface 62. The panel 58 is attached to the body side liner or top sheet 32 by any well-known method, e.g., thermal or ultrasonic bonding or adhesive bonding, along its top edge immediately below or along the back edge of the diaper. When so mounted the panel 58 forms a flap which is arranged to be moved or pivoted upward from a inoperative position (shown by the solid lines in FIG. 2), to an operative position (shown by the phantom lines in FIG. 2) to expose a body-friendly adhesive track or stripe 64 located on the flap's inner surface 62.

The adhesive stripe 64 is a pressure sensitive adhesive, which when exposed can be readily attached to the body of the wearer by engagement therewith under slight pressure. This engagement, to be described later, forms a liquid-impervious seal or interface between the flap 58 and the skin of the wearer at the back waist portion of the diaper to prevent the egress of liquid fecal waste therefrom. Moreover, with the adhesive secured to the skin of the wearer, the flap 58 can move or flex when the wearer moves thereby providing some "give," tending to ensure that the adhesive securement to the skin is not accidentally broken. The adhesive is a pressure-sensitive composition which is body-friendly" so as to be non-irritating and may be formulated from a wide range of polymeric chemical compounds formulated with extender oils, tackifying resins and mineral fillers. In this execution, the adhesive is a soft compliant pressure sensitive with high tack and low peel properties for removable applications, suitable for direct use on skin with minimal removal discomfort. It is generally applied at high coating weights to take advantage of its high compliance. The viscosity range for this adhesive is 277,500 cps@275° F. and 1,745 cps@375° F. and applied at process temperatures of 290–350° F. Most preferred in the present invention is the pressure sensitive adhesive 10127-32-5 available from National Starch and Chemical Company, Bridgewater, N.J.

The pressure sensitive adhesive stripe 64 preferably extends across virtually the full idth of the flap 58. The flap is normally held in its closed or inoperative position by the engagement of the adhesive stripe 64 to a release coating (not shown) which is on the inner surface of the topsheet 32 under the flap. The release coating may be formed of a layer of any suitable non-stick material, e.g., a silicone. When the flap 58 is in its normally closed or inoperative position the adhesive stripe 64 releasably engages the release coating to hold the flap in place as shown in FIG. 2. This action protects the adhesive from contamination from fibers or other materials which could interfere with its adhesive properties until it is ready to be used.

It should be clear to those skilled in the art that depending upon the material making up the topsheet 32, a release layer or coat may not be necessary on the topsheet 32 for the adhesive stripe 64 to be releasably secured thereto. In this regard, the adhesive stripe 64 may directly engage the material forming the topsheet 32, providing that it can be readily peeled therefrom and will not be contaminated by any fibers or other material of the topsheet which might tend to detract from its ability to adhere to the skin of the wearer.

If it is desired to make use of the flap to form the barrier wall with the wearers skin, all that is required is to grasp the flap 58 from its bottom edge to unpeel the adhesive stripe 64 off of the release layer. The flap 58 can then be extended upward, like shown by the phantom lines in FIG. 2, to thereby expose the adhesive stripe 64. Once the adhesive stripe 64 is exposed it can be brought into adhesive securement with the contiguous skin of the wearer, such as shown in FIG. 3, by the application of slight pressure on the outer surface of the flap. This adhesive securement forms a liquid-impervious interface between the adhesive and the skin along a major length of the back waist portion of the diaper 20. As will be appreciated by those skilled in the art the term "adhesively secured to the body of the wearer" as used in this application refers to the establishment of intimate contact between the polymeric pressure sensitive adhesive and an epithelial layer of skin. The term "intimate contact" more specifically refers to an adhesive bond formed between the adhesive and the skin. In the context of the present invention, this bond has sufficient strength to block the outward migration of bodily fluid. Furthermore, the adhesive bond should have sufficient wet strength in the presence of bodily fluids such as urine and feces to maintain intimate contact between the adhesive and skin layer during the entire time period that the diaper remains on the wearer.

In view of the disposable nature of the diaper of the present invention, it is should be clear that the adhesive bond between the pressure sensitive adhesive 64 and the layer of skin of the wearer's body necessarily is readily and easily disrupted and broken upon intentional removal of the diaper. Moreover, the breaking of the adhesive bond is carried out with minimal damage to and removal of the epithelial layer of skin which had been in contact with the adhesive. Furthermore, during the period of time when intimate contact between the pressure sensitive adhesive and the skin is established and maintained, it is an important requirement that substantially no inter-diffusion of any potentially irritating chemical component of the adhesive into the skin layer occur. To that end, the pressure sensitive adhesive of the present invention is selected with the objective of providing three important functional requirements. In particular, it should exhibit the ability to maintain, during the entire wear period of the garment and in the presence of heat and moisture, an intimate bond with the wearer's skin, thus providing a barrier to the outward migration of bodily waste material. It should also exhibit the ability to provide a bond with the skin which is readily broken upon removal of the garment without significant removal of or injury to the epithelial layer of skin in contact with the adhesive. Lastly, it should exhibit an absence of significant inter-diffusion of constituents (whether present in the adhesive or formed in the adhesive during usage) into the skin layer, since such action could lead to skin irritation, redness, swelling or any allergic reaction or sensitization.

In FIG. 4 there is shown an alternative embodiment of a diaper 100 constructed in accordance with this invention. The diaper 100 is identical to the diaper 20 except for the fact that it does not include the heretofore identified standing leg cuffs 52, but does include an optional front barrier wall flap 102 at the waist to prevent the egress of liquid fecal waste from that region. In the interest of brevity the common components of diaper 100 will be given the same reference numbers as given with respect to the diaper 20 and no further description of the details and operation of the diaper 100 will be made herein. Suffice it to state that the rear flap 58 of the diaper 100 is used in the same manner as described with respect to diaper 20 to form a liquid-proof seal at the back waist portion of the diaper. The front flap 102 is constructed identically or near to the rear flap 58. Thus it includes an adhesive stripe 64 on its undersurface 62. The front flap is used in the same manner as the rear flap to adhesively engage the skin of the wearer in the lower abdominal region to prevent the egress of liquid waist therefrom.

It should be pointed out at this juncture that the use of either or both flaps is completely optional with the user. Thus, if adhesive securement of the diaper to the skin isn't desired, the flaps 58 and 102 can be left in their closed or inoperative position, whereupon the adhesive stripes 64 will be covered so that they do not engage the skin of the wearer.

If adhesive securement is desired at the front waist section in addition to at the rear waist section, the garment may optionally include some elastic means in the waist between the front and back. Such elastic can provide some "give" to ensure that neither the front or back (and especially the back) adhesive seal is accidentally broken when the wearer moves about with the diaper on.

In FIGS. 5–7 there is shown another alternative disposable diaper 200 constructed in accordance with the subject invention. The common features of diapers 20, 100 and 200 will be given the same reference numbers and their details will not be reiterated in the interest of brevity. In FIGS. 5 and 6 only the inner surface of the diaper 200 at the back waist region 24 is shown. That portion of the diaper includes an alternative barrier wall forming a "containment pocket" for precluding the egress of liquid fecal waste from the back waist portion of the diaper. As can be seen in FIGS. 5 and 7 the containment pocket is made up of a rectangular panel 202 constructed of a liquid impervious material, e.g., a poly laminate material under the model designation XLAM 9B-396, which is adhesively secured on three sides to the diaper's topsheet 32 at the back waist portion 24. In particular, the panel 202 is fixedly secured along its top edge 204 and two side edges 206 and 208 to the topsheet 32. The lower edge 210 of the panel 202 is left unattached, thereby forming a pocket opening 212 (FIG. 7) thereat. As shown in FIG. 5, the outer surface of the containment pocket forming panel 202 has a strip of pressure sensitive adhesive 64, like that described above, located thereon. This adhesive stripe 64 serves to secure the panel 202 of the diaper to the skin of the wearer in the waist region, if such action is desired by the user. In this regard, as discussed with reference to the embodiments 20 and 100, the use of the adhesive securement of the containment pocket 202 to the skin of the wearer is optional, albeit desirable. Thus, the diaper may be used with the containment pocket not adhesively secured to the skin. In such a case, a peelable cover strip 214 is left releasably secured over the adhesive stripe 64. The outer surface of the cover strip is left preferably formed of soft, pliable, skin-friendly material, such as woven, knit or non-woven textiles with a pleasing texture. Additionally, polymeric foams or film are suitable, as well as composites selected from among fibers, film, foam, and paper or any combination. The inner surface or layer of the cover strip is coated with a release coating, e.g., a silicone, to enable the cover strip to be readily peeled from the adhesive stripe when desired to adhesively secure the diaper to the wearer. If such adhesive securement is not desired the diaper can be worn with the cover strip 214 in place. In such a case, the cover sheet provides a comfortable interface for the wearer. The cover sheet when in place on the adhesive stripe also serves to protect it from contaminants so that its adhesive properties are maintained until ready for use.

The diaper 200 is mounted on the wearer in the same manner as described with reference to diaper 20. If it is desired to make use of the adhesive stripe 64 to secure the containment pocket 202 to the skin of the wearer, all that is required is to peel off the cover strip 214 from the adhesive strip 64, thereby exposing the stripe. Slight pressure on the diaper to bring the adhesive stripe into contact with the skin is all that is necessary to form the adhesive securement of the containment pocket 202 with the skin. When so secured any liquid waste material will be trapped under and inside the pocket and will be precluded from egress therefrom by the good liquid-resistant adhesive seal between the adhesive stripe and the skin of the wearer as shown in FIG. 7.

Figure 8:
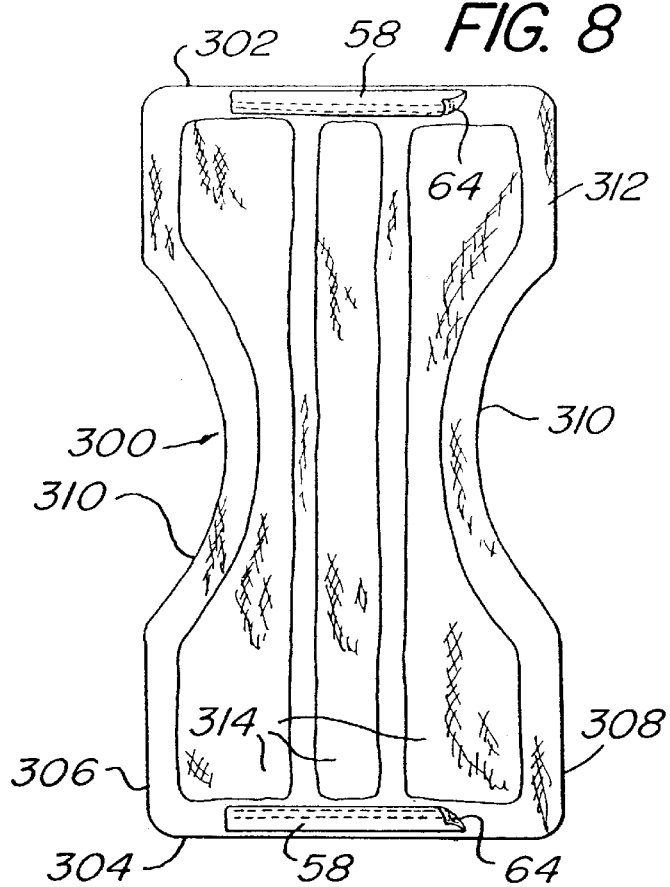
FIG. 8 is a reduced plan view of another preferred embodiment of one type of disposable absorbent article, e.g., a "regular" absorbent shield, constructed in accordance with this invention to provide a fecal material barrier at the waist.

In FIG. 8 there is shown another alternative disposable absorbent article 300 constructed in accordance with this invention. That article is a "regular" type incontinent shield. The incontinent shield basically comprises a generally rectangular member having a rear waist portion 302, a front waist portion 304 and a pair of side portions 306 and 308. Each of the side portions includes a respective arcuate recess 310 therein to accommodate the respective legs of the wearer when the shield is in place. The shield 300 comprises a topsheet 312, a correspondingly shaped outer cover or backsheet and an interposed core 314. The inner sheet 312 is formed of a moisture pervious material, e.g., spunbond polypropylene with surfactant treatment while the outer sheet (not shown) is formed of a moisture impervious material, e.g., polyethylene film or poly laminate. The core 314 is formed of a moisture absorbent material e.g., pulp and superabsorbent particulate and in the embodiment shown includes three sections, a central elongated section and two side sections. The layers of material forming the shield are bonded together along their peripheral edges and along two longitudinally extending lines separating the three sections of the core from one another. A strip of pressure sensitive tape (not shown) is provided on the outer cover and extends longitudinally therealong. The strip of adhesive is in turn covered by a releasable peel strip (not shown). The peel strip is formed of paper having a release liner, e.g., silicone, on its inner surface and is arranged to engage the pressure sensitive adhesive. With the peel strip removed, the adhesive strip on the outer cover is exposed so that the shield 300 can be adhesively mounted within an undergarment.

The shield 300 is provided with a pair of barrier wall flaps 58, like those discussed heretofore. Each of the flaps 58 is of identical or near to construction and basically comprises a rectangular panel having an outer surface 60 and an inner surface 62. An adhesive stripe 64, like that described heretofore, is provided on the inner surface 62 of each flap. One of the flaps 58 is mounted on the rear waist portion 302 with the top edge of the flap being fixedly secured, e.g., bonded, to the top sheet 312 immediately adjacent the edge of the rear waist section. In a similar manner, the flap 58 is mounted on the front waist section 304. Operation of the flaps 58 is as described, and hence will not be reiterated herein.

In FIG. 9, there is shown another alternative disposable absorbent article 400 constructed in accordance with this invention. The article 400 is a "belted" undergarment. The belted undergarment is of generally rectangular shape having a rear waist portion 402, a front waist portion 404 and a pair of linear sides 406 and 408. The undergarment is made up of a topsheet 410 formed of a moisture-pervious material, e.g., spunbond polypropylene with surfactant treatment, an outer cover or sheet (not shown) formed of a moisture impervious material, e.g., polyethylene film or poly laminate, and a core of generally rectangular shape and formed of a highly moisture absorbent material, e.g., pulp and superabsorbent particulate. The topsheet and the outer cover are bonded to each other about their entire periphery, with the core 412 interposed therebetween. The sides 406 and 408 of the garment 400 are elasticized by any suitable means, e.g., elastic threads 414. A reinforced slit or slot 416 is provided in each corner of the undergarment to accommodate a respective button of an elastic support strap (not shown). In particular, two support straps are used to hold the article 400 in place. Each strap has a button at each of its ends. In use, the button on one end of one strap is extended through one of the slits 416 on one side of the garment 400 and the button on the other end of that strap is extended through the other slit 416 on that side of the garment 400. The other support strap is similarly connected to the other side of the garment to hold the garment in place on the wearer, with the rear or back waist portion 402 located at the wearer's lower back-buttocks region and the front waist portion 404 being located at the wearer's lower abdominal region.

Like the embodiments described earlier, the belted undergarment 400 also includes a pair of barrier wall forming flaps 58 with adhesive strips 64 constructed like those described heretofore. Each of the flaps 58 is mounted on its respective waist portion in the same manner as described with reference to the embodiment 300 of FIG. 8 and can be used in the same manner.

In FIG. 10, there is shown yet another alternative disposable absorbent article 500 constructed in accordance with this invention. The article 500 is an "extra absorbent" type beltless incontinent pad. The pad 500 is generally rectangular in shape having a rear waist portion 502, a front waist portion 504 and a pair of linear side portions 506 and 508. The pad 500 includes a topsheet 510 formed of a moisture pervious material, e.g., spunbond polypropylene with surfactant treatment, an outer cover (not shown) formed of a moisture impervious material, e.g., polyethylene film or poly laminate, and an interposed core 512, formed of an absorbent material, e.g., pulp and superabsorbent particulate. The topsheet is bonded to the outer cover about its entire periphery, with the core 512 interposed therebetween. The sides 506 and 508 are elasticized along their length with elastic threads 514. The outer surface of the outer layer includes a longitudinally extending pressure sensitive adhesive strip covered by a removable peel strip 516. When the peel strip is removed, the pressure sensitive adhesive is exposed to enable the extra absorbent pad to be adhesively secured to an undergarment. When the garment with the pad is in place on the wearer the rear waist portion 502 is located at the lower back-buftocks region of the wearer and the front waist portion 504 is located at the lower abdomen of the wearer.

Like the embodiments discussed earlier, the extra absorbent pad 500 also includes a pair of barrier forming flaps 58 each including a stripe of adhesive 64. Each of the flaps 58 with the adhesive stripe 64 is constructed in an identical manner to that described heretofore and is mounted on the topsheet 510 in the same manner as described heretofore. As also described heretofore, each of the flaps can be used, if desired, to expose the adhesive to adhesively secure the respective portion of the waist of the pad 500 to the adjacent surface of the skin.

Figure 11:
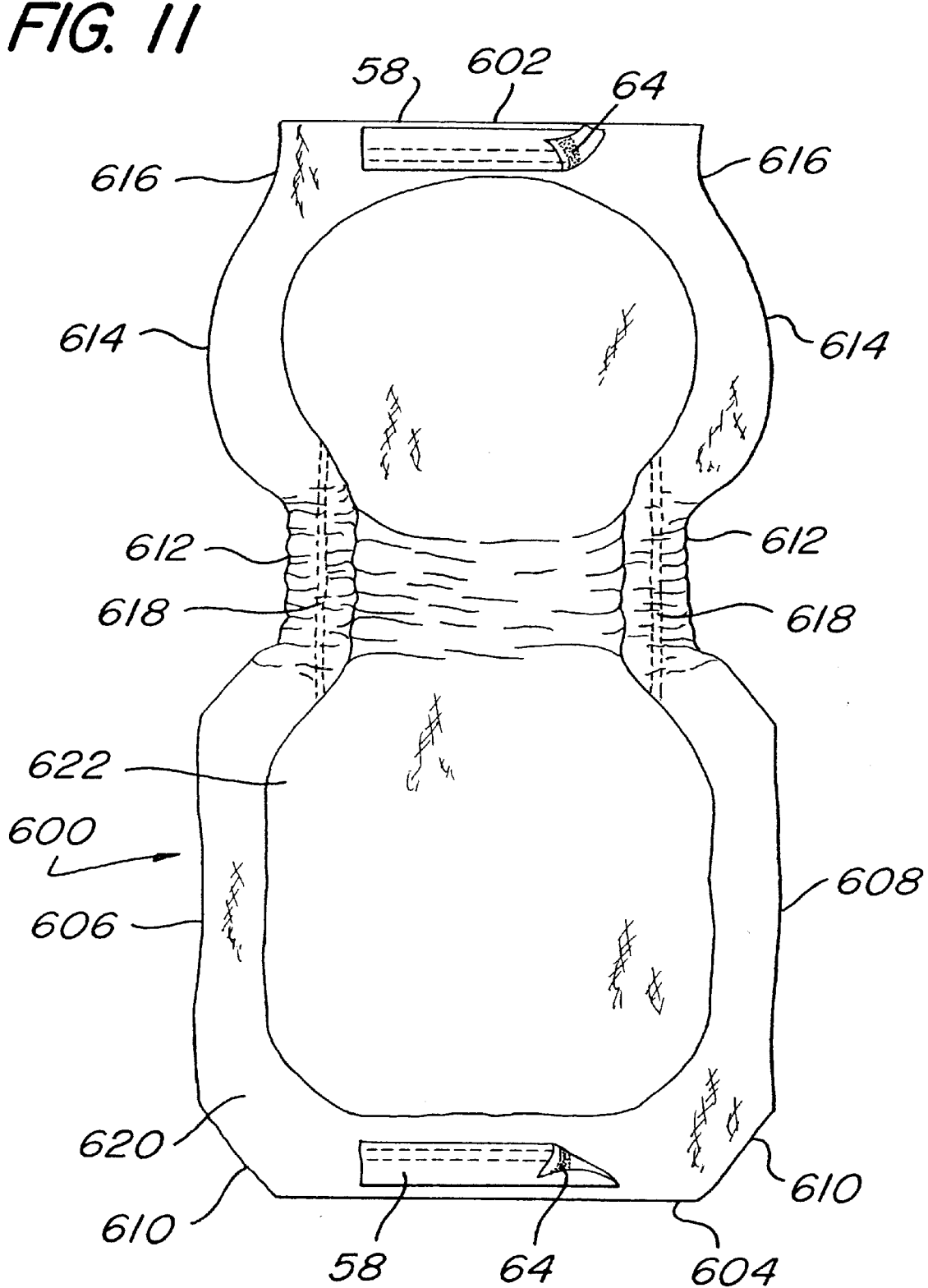
FIG. 11 is a reduced plan view of yet another preferred embodiment of one type of disposable absorbent article, e.g., an absorbent insert, constructed in accordance with this invention to provide a fecal material barrier at the waist.

In FIG. 11, there is shown yet another alternative disposable absorbent article constructed in accordance with this invention. That article is an absorbent "insert" 600. The absorbent insert 600 includes a front waist portion 602, a rear waist portion 604 and a pair of sides 606 and 608. The sides 606 and 608 each include a diagonally extending section 610 at the interface with the rear waist portion 604, a concave arcuate intermediate portion 612, a convex portion 614 and a convex section 616 at the interface with the front waist portion 602. The side portions 612 are elasticized by means longitudinally extending elastic threads 618. This feature gathers the absorbent insert 600 at the section 612. The absorbent insert 600 includes a topsheet 620 formed of a moisture pervious material, e.g., spunbond polypropylene with surfactant treatment, an outer cover (not shown) formed of a moisture impervious material, e.g., polyethylene film or poly laminate, and a core 622 formed of a liquid absorbent material, e.g., pulp and superabsorbent particulate. The topsheet 620 and the outer cover (not shown) are bonded to each other along their entire periphery, with the absorbent core 622 interposed therebetween. The shape of the core 622 basically conforms to the shape of the topsheet and backsheet, except that it is slightly smaller along the entire perimeter.

The absorbent insert 600 also includes a pair of barrier wall forming flaps 58 each with an adhesive stripe 64 constructed like that described heretofore. One of the flaps 58 is fixedly secured to the topsheet 620 immediately adjacent the back waist portion 604 and while the other is similarly secured to the front waist portion 602. The flaps may be used, if desired, as described heretofore.

As should be appreciated by those skilled in the art from the foregoing, the present invention responds to the need for disposable articles, such as diapers and related absorbent products, by providing enhanced protection and improved containment properties, particularly with regard to fecal matter. In accordance with the teachings of this invention, selected segments in the waist region of the garment may, if desired, be adhesively secured to body of the wearer, thereby forming a barrier to the flow of loose fecal matter through the waist of the garment.

The adhesive used is body-friendly so that it makes a good liquid resistant seal, which is comfortable, non-irritating, and resistant to accidental breakage, yet can be readily broken when desired to remove the article from the wearer.

Without further elaboration the foregoing will so fully illustrate our invention that others may, by applying current or future knowledge, adopt the same for use under various conditions of service.

We claim:

1. A disposable absorbent article arranged to be worn by a living being to trap and collect loose or liquid waste of the being, said article comprising an absorbent chassis, a first barrier panel, and a first selectively exposable skin-friendly adhesive, said chassis having a back waist portion, a crotch portion, a front waist portion, and an inner surface, said chassis being configured to be worn between the legs of the being with said inner surface directed toward the being's skin, said first barrier panel comprising a flap mounted on said inner surface of said chassis at said back waist portion, said flap having a outer surface and an inner surface, said first selectively exposable, skin-friendly adhesive being located on said inner surface of said flap for releasable engagement with said inner surface of said chassis to hold said flap against said inner surface of said chassis, whereupon said flap covers and protects said first selectively exposable, skin-friendly adhesive, said flap being arranged to be moved from said position against said inner surface of said chassis to an operative position wherein said first selectively exposable, skin-friendly adhesive is exposed and oriented for engagement with the adjacent skin of the being, whereby said flap and said first selectively exposable, skin-friendly adhesive form a liquid-resistant seal with the being's skin to thereby impede the egress of the loose or liquid waste from said back waist portion.

2. The disposable absorbent article of claim 1 wherein said outer surface of said flap comprises a skin-friendly cover.

3. The disposable absorbent article of claim 1 wherein said flap is fluid impervious.

4. The disposable absorbent article of claim 3 wherein said flap is vapor permeable.

5. The disposable absorbent article of claim 3 wherein said flap is hydrophobic.

6. The disposable absorbent article of claim 1 additionally comprising fastening means operable to secure said article in place on the being's body.

7. The disposable absorbent article of claim 6 wherein said fastening means are located at said waist portions.

8. The disposable absorbent article of claim 7 wherein said fastening means comprise a pair of fastening tabs extending from the back waist portion, and a landing zone on said front waist portion arranged to receive said fastening tabs.

9. The disposable absorbent article of claim 8 wherein said fastening tabs and said landing zone include multihooks and multiloops arranged to releasably engage each other.

10. The disposable absorbent article of claim 8 wherein said fastening tabs comprise an adhesive for releasable securement to said landing zone.

11. The disposable absorbent article of claim 1 additionally comprising standing leg gathers located adjacent said crotch portion.

12. A disposable absorbent article arranged to be worn by a living being to trap and collect loose or liquid waste of the being, said article comprising a flexible chassis, fastening means, a first barrier panel, and a first selectively exposable skin-friendly adhesive, said chassis including an outer cover, and inner layer, and an absorbent core interposed therebetween, said chassis having a back waist portion, a crotch portion, and a front waist portion and chassis being configured to be worn with said crotch portion between the legs of the being and with said inner layer directed toward the being's skin, said fastening means being arranged to cooperate with each other to hold said article in place on the being, said first barrier panel comprising a flap mounted on said inner surface of said body member at said back waist portion, said flap having an outer surface and an inner surface, said first selectively exposable, skin-friendly adhesive being located on said inner surface of said flap for releasable engagement with said inner layer of said chassis to hold said flap against said inner layer of said chassis, whereupon said flap covers and protects said first selectively exposable, skin-friendly adhesive, said flap being arranged to be moved from said position against said inner layer of said chassis to an operative position wherein said first selectively exposable, skin-friendly adhesive is exposed and oriented for engagement with the adjacent skin of the being, whereby said flap and said first selectively exposable, skin-friendly adhesive form a liquid-resistant seal with the being's skin to thereby impede the egress of the loose or liquid waste from said back waist portion.

13. The disposable absorbent article of claim 12 wherein said outer surface of said flap comprises a skin-friendly cover.

14. The disposable absorbent article of claim 12 wherein said flap is fluid impervious.

15. The disposable absorbent article of claim 14 wherein said flap is vapor permeable.

16. The disposable absorbent article of claim 14 wherein said flap is hydrophobic.

17. The disposable absorbent article of claim 12 wherein said fastening means are located at said waist portions.

18. The disposable absorbent article of claim 17 wherein said fastening means comprise a pair of fastening tabs extending from the back waist portion, and a landing zone arranged to receive said fastening tabs, said landing zone being located on said front waist portion.

19. The disposable absorbent article of claim 18 wherein said fastening tabs and said landing zone include multihooks and multiloops arranged to releasably engage each other.

20. The disposable absorbent article of claim 18 wherein said fastening tabs comprise an adhesive for releasable securement to said landing zone.

21. The disposable absorbent article of claim 12 wherein said outer cover forms a liquid impervious barrier.

22. The disposable absorbent article of claim 21 wherein said inner layer is liquid permeable.

23. The disposable absorbent article of claim 12 wherein said inner layer is liquid permeable.

24. The disposable absorbent article of claim 12 additionally comprising standing leg gathers located adjacent said crotch portion.

25. The disposable absorbent article of claim 12 additionally comprising a second barrier panel located on said front waist portion and on which a second selectively exposable skin-friendly adhesive is located, said second barrier panel comprising a second flap mounted on said inner layer of said chassis and having an inner surface and an outer surface, said second selectively exposable, skin-friendly adhesive being located on said inner surface of said second flap for releasable engagement with said inner layer of said chassis to hold said second flap against said inner layer of said chassis, whereupon said second flap covers and protects said second selectively exposable, skin-friendly adhesive, said flap being arranged to be moved from said position against said inner layer of said chassis to an operative position wherein said second selectively exposable, skin-friendly adhesive is exposed and oriented for engagement with the adjacent skin of the being, whereby said flap and said second selectively exposable, adhesive to form a liquid-resistant seal with the being's skin to thereby impede the egress of the loose or liquid waste from said front waist portion.

26. The disposable absorbent article of claim 12 wherein said article comprises a diaper.

27. The disposable absorbent article of claim 26 wherein said article additionally comprises elastic standing leg cuffs.

28. The disposable absorbent article of claim 12 wherein said article comprises a belted undergarment having plural openings for connection to a support belt.

29. The disposable absorbent article of claim 12 wherein said article comprises an absorbent shield having an adhesive located on said outer cover for mounting said absorbent shield in a garment.

30. The disposable absorbent article of claim 12 wherein said article comprises an absorbent insert having an adhesive located on said outer cover for mounting said absorbent shield in a garment.

* * * * *